(12) United States Patent
Hölzl

(10) Patent No.: US 8,493,065 B2
(45) Date of Patent: Jul. 23, 2013

(54) DEVICE AND METHOD FOR INDUCTIVE MEASUREMENTS—SIGNAL RECONSTRUCTION

(75) Inventor: Roland Hölzl, Munich (DE)

(73) Assignee: Prueftechnik Dieter Busch AG, Ismaning (DE)

( * ) Notice: Subject to any disclaimer, the term of this patent is extended or adjusted under 35 U.S.C. 154(b) by 605 days.

(21) Appl. No.: 12/783,713

(22) Filed: May 20, 2010

(65) Prior Publication Data

US 2010/0295545 A1    Nov. 25, 2010

(30) Foreign Application Priority Data

May 20, 2009    (DE) .................. 10 2009 022 138

(51) Int. Cl.
     *G01N 27/82*      (2006.01)
(52) U.S. Cl.
     USPC ............................................ 324/238; 702/38
(58) Field of Classification Search
     USPC ............... 324/164, 204, 241, 500; 702/38, 702/84
     See application file for complete search history.

(56) References Cited

U.S. PATENT DOCUMENTS

| | | | |
|---|---|---|---|
| 4,209,744 A | 6/1980 | Gerasimov et al. | |
| 4,445,088 A | 4/1984 | Schübel | |
| 5,175,498 A | 12/1992 | Cueman et al. | |
| 7,423,424 B2 * | 9/2008 | Hoelzl et al. | 324/240 |
| 2004/0066189 A1 * | 4/2004 | Lopez | 324/238 |
| 2009/0051350 A1 | 2/2009 | Becker et al. | |
| 2010/0295551 A1 * | 11/2010 | Holzl | 324/500 |

FOREIGN PATENT DOCUMENTS

| | | |
|---|---|---|
| DE | 40 03 330 A1 | 8/1991 |
| EP | 1 189 058 A2 | 3/2002 |
| EP | 1 017 577 B1 | 11/2002 |
| GB | 2 192 064 A | 12/1987 |
| WO | 95/16912 A1 | 6/1995 |
| WO | 01/22075 A2 | 3/2001 |
| WO | 2006/007826 A1 | 1/2006 |

OTHER PUBLICATIONS

Curt Schurgers and Mani B. Srivastava; A Systematic Approach to Peak-To-Average Power Ratio in OFDM; Electrical Engineering Department, University of California at Los Angeles (UCLA); In: Proc. SPIE 47TH Annu. Meeting, 201, S. 454ff.
Zoran Cvetkovic and Martin Vetterli; On Simple Oversampled A/D Conversion in L2 (IR); IEEE Transactions on Information Theory, vol. 47, No. 1, Jan. 2001, pp. 146-154.
Farokh Marvasti, Moh'D Hasan, M. Echhart, and Siamak Talebi; Efficient Algorithms for Burst Error Recovery Using FFT and Other Transform Kernels; IEEE Transactions on Signal Processing, vol. 47, No. 4, Apr. 1999, pp. 1065-1075.

* cited by examiner

*Primary Examiner* — Arleen M Vazquez
*Assistant Examiner* — Alesa Allgood
(74) *Attorney, Agent, or Firm* — Roberts Mlotkowski Safran & Cole, P.C.; David S. Safran

(57) ABSTRACT

Method and device for nondestructive and noncontact detection of faults in a test piece, or electrically conductive particles in a liquid flow, moving past the device, using eddy currents. The test piece or flow is exposed to periodic alternating electromagnetic fields. A periodic electrical signal is detected by a receiver coil. The receiver coil signal has a carrier oscillation whose amplitude and/or phase is modulated by defects in the test piece or by electrically conducting particles and is digitized. A useful signal is produced from the digitized receiver coil signal, and the useful signal is evaluated with an evaluation unit to detect faults in the test piece or electrically conductive particles. When overdriving of the A/D converter stage by the receiver coil signal is ascertained, a part of the receiver coil signal truncated by the A/D converter stage is reconstructed using a mathematical approximation in the digitized receiver coil signal.

7 Claims, 4 Drawing Sheets

DEVICE AND METHOD FOR INDUCTIVE MEASUREMENTS—SIGNAL RECONSTRUCTION

BACKGROUND OF THE INVENTION

1. Field of the Invention

This invention relates to a device and method for nondestructive and noncontact detection of faults in a test piece. In particular, the present invention relates to fault detection using measurements of an eddy current or magnetic flux leakage. Furthermore, the invention relates to a device and a method for detecting electrically conductive particles in a liquid flowing in a pipe segment using the eddy currents induced in the particles being detected.

2. Description of Related Art

Conventional nondestructive and noncontact detection of faults in a test piece of a semi-finished metallic product is performed by inducing and measuring eddy currents in the test piece. In doing so, the test piece is exposed to periodic alternating electromagnetic fields through a sinusoidally energized transmitter coil. The resulting eddy currents induced in the test piece induce a periodic electrical signal in a coil arrangement which is used as a probe. This periodic electrical signal has a carrier oscillation according to the transmitter carrier frequency whose amplitude and/or phase is modulated by a fault in the test piece when a fault travels into the sensitive region of the probe. Conventionally, when scanning the test piece, the test piece is moved linearly with respect to the probe; however, arrangements with a rotating probe also known. For example, an eddy current measurement device with a linearly advanced test piece is described in U.S. Pat. No. 5,175,498.

Similarly, electrically conductive particles in a liquid, which flows through the coils, cause eddy current losses. These eddy currents can be determined by measuring the impedance change of the coils. In this way electrically conductive particles in a liquid flowing in a pipe can be detected by means of an inductive coil arrangement. This is especially advantageous for detection of the concentration of metallic particles in the lubricant circuit of a machine in order to draw conclusions about the machine state such as measurements of machine wear.

Another conventional measurement method for nondestructive and noncontact detection of faults in a test piece is magnetic flux leakage measurement (or stray magnetic field measurement), by means of an induction coil with a magnetic yoke, which magnetizes the test piece resulting in a magnetic flux leakage produced by the test piece. The magnetic flux is measured by means of a suitable sensor. Faults in the test piece are detected based on their effects on the magnetic flux leakage. One example of this flux leakage measurement can be found in U.S. Pat. No. 4,445,088.

In eddy current measurement devices containing probes which rotate around the periphery of the test piece, measuring the distance between the probe head and test piece is performed in order to correct the measurement with respect to the distance because the distance fluctuates during the course of one revolution. The measurement of the distance is performed because of decentering or asymmetry of the cross section of the test piece occurs during one revolution. One example of this arrangement can be found in German Patent Application No. 40 03 330 A1.

International Patent Application Publication WO 2006/007826 A1 discloses an eddy current measurement device with a digital front end, such that the A/D converter stage is triggered with a n-th integral fraction of the frequency of the carrier oscillation, where n is selected depending on the fault frequency, i.e., the quotient of the relative velocity between the test piece and probe and the effective width of the probe.

U.S. Pat. No. 4,209,744 describes an eddy current measurement device which has a test means which simulates signals that are typical of faults in a test piece in order to perform fundamental checking of the electronics. However, only a single amplitude and a defined primary fault frequency can be simulated. Even if the simulated fault signal were provided with variations, all the electronics cannot be tested. Furthermore, such a simulated fault signal cannot be traced to a certified reference element without dismounting all the electronics and sending them to a laboratory.

International Patent Application Publication WO No. 01/22075 A2 describes an eddy current measurement device within the framework of self-calibration of the system. The intensity of the signal originates from a segment of a test piece which does not contain a fault.

GB Patent Application No. 2 192 064 describes an inductive test device where the device is detuned to simulate a fault by a self-test means and by connecting a LED.

SUMMARY OF THE INVENTION

A primary object of this invention is to devise a device and method for nondestructive and noncontact detection, especially by means of eddy current measurement, or flux leakage measurement, of faults in a test piece or by detecting electrically conductive particles in a liquid flowing in a pipe segment, to ensure that measurement is as reliable as possible.

This object is achieved by the features of the disclosed embodiments as described herein.

According to aspects of the invention, it is advantageous that, when overdriving the A/D converter stage by the receiver coil signal is ascertained by the signal processing unit through monitoring the curve shape of the digitized receiver coil signal, the part of the receiver coil signal which has been truncated by the A/D converter stage is reconstructed with a mathematical approximation in the digitized receiver coil signal. This feature results in savings in the required hardware, especially since, as a result of signal reconstruction, the demands on the dynamics of the A/D converter are reduced and a more economical A/D converter can be used. Ultimately, the measurement range dictated by the hardware can be expanded by software as a result of this signal reconstruction. Furthermore, when the A/D converter has been overdriven due to the failure of a component, a fault which occurred in the test piece can still be quantitatively detected through signal reconstruction, enhancing the opportunities for promptly locating faults.

Preferably, the A/D converter can be triggered, the digitized and optionally reconstructed receiver coil signal which is filtered by frequency filters in order to obtain a demodulated useful signal, and the A/D converter stage is triggered with a n-th integral fraction of the frequency of the carrier oscillation of the signal for the transmitter coil arrangement, where n depends on the fault frequency which arises as a quotient of the relative velocity between the test piece and the receiver coil arrangement and the effective width of the receiver coil arrangement, and the frequency filters are set as a function of the fault frequency.

DETAILED DESCRIPTION OF THE INVENTION

Figure 1:
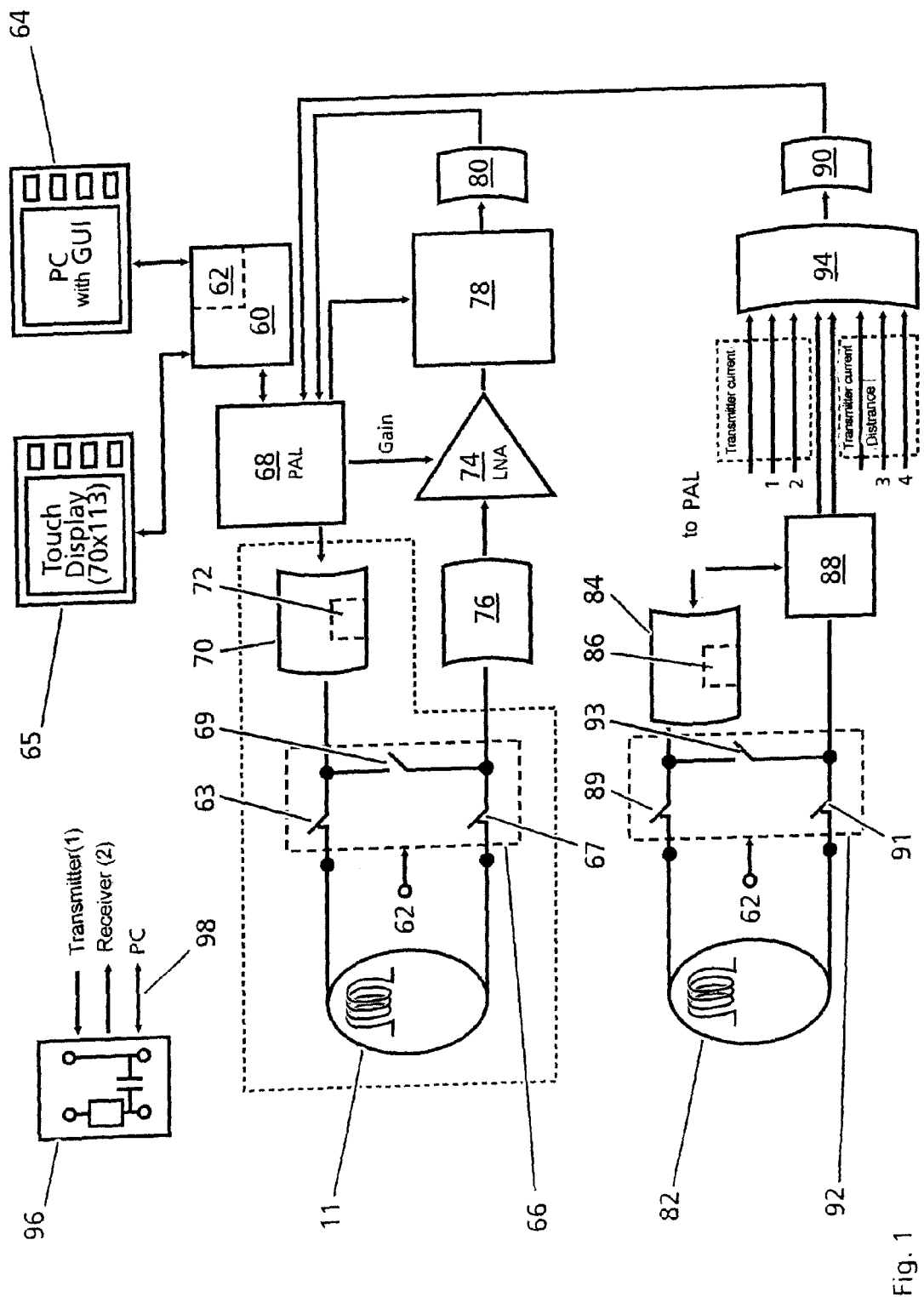
FIG. 1 is a block diagram of an inductive measurement device with a self-test function and calibration function in accordance with the invention.

FIG. 1 shows a block diagram of an inductive measurement device with a self-test function and calibration function according to an aspect of the invention. A signal processor 60 communicates with a programmable array logic (PAL) element 68. The PAL element 68 is designed to control the A/D converter and D/A converter. The PAL element 68 also supplies a transmitter coil driver 70 which is provided with a current sensor 72, and delivers the signal for the transmitter coil arrangement (not shown in FIG. 1) of the probe 11 (i.e., measurement head). The receiver coil signal of the receiver coil arrangement (not shown in FIG. 1) of the probe 11 is provided to a low-noise amplifier 74 which is used as a preamplifier. The gain of the low-noise amplifier 74 is controlled or variably set by the processor 60 by way of the PAL element 68. The signal amplified by the amplifier 74 passes through a resonance filter 78 and is supplied to the PAL element 68 and then to the processor 60 for processing, or evaluation, of the signal after digitization in an A/D converter 80, which can be designed to handle 18 bits. In this way, from the receiver coil signal a usable signal is produced which is then evaluated by an evaluation unit. The evaluation unit can be implemented in the form of the processor 60 and/or externally, for example, as a personal computer (PC) 64.

Furthermore, the system can have a distance sensor 82 with a transmitter coil and a receiver coil (not shown) in order to produce a distance signal from the receiver coil signal of the distance sensor 82. The distance signal constitutes a measure of the distance between the test piece and the probe 11. There is a driver 84 for the transmitter coil of the distance sensor 82 which has a current sensor 86 and which is supplied by the PAL element 68. The receiver coil signal of the distance sensor 82 is supplied to a unit 88 which performs amplification, offset and rectification of the distance signal. The unit 88, like the amplifier 74, is controlled by the PAL element 68. The distance signal is supplied to the PAL element 68, and then to the processor 60 for evaluation by an A/D converter 90, which can be designed to handle 16 bits. Further, there can be several distance sensors 82.

The elements 68, 70, 74, 76, 78, 80, and optionally 60, as well as elements 84, 86, 88, 90 are part of the signal processing unit which produces a signal for evaluation by the evaluation unit from the receiver coil signals.

A self-test unit 62 is implemented in the processor 60. The self-test unit 62 performs systematic quantitative checking of the signal processing functions of the signal processing unit of the front end and systematic quantitative checking of the probe 11 and of the distance sensor 82. Further, the processor 60 performs the checking automatically, at system startup, or at the request of the user interface which can be PC 64 or a touch display 65.

A switch arrangement 66 with three switches 63, 67, 69 is used for monitoring the signal processing unit. The three switches 63, 67, 69 can be actuated by the self-test unit 62 (in doing so the switches 63 and 67 are opened and the switch 69 is closed) in order to feed the signal for the transmitter coil of the probe 11 as a periodic input signal into the signal processing unit, i.e., into the input of the amplifier 74 by bypassing the transmitter coil directly.

In the self-test, the self-test unit 62 provides the signal for the transmitter coil which is varied with respect to frequency and amplitude in order to check whether the measured gain of the amplifier 74 and the measured corner frequencies and steepness of the frequency filter 78 are within the required specifications. A corresponding fault signal is output to the user interface 64, 65 if the specification is not satisfied.

According to aspects of the invention, the device can be made with several channels. Transmitter coil driver 70, the probe 11 and the self-monitoring switch arrangement 66 are provided once for each channel and a multiplexer 76 is connected upstream of the amplifier 74 (for each transmitter coil there is then its own frequency).

A self-test switch arrangement 92 is provided between the driver 84 and the unit 88. The self-test switch arrangement 92 has three switches 89, 91, 93 which can be actuated by the self-test unit 62 (in doing so the switches 89 and 91 are opened and the switch 93 is closed) to induce a self-test of the unit 88, or of the A/D converter 90 by a signal which is output by the transmitter coil driver 84, and which is bypassing the transmitter coil of the distance sensor 82. This signal is being sent directly to the input of the unit 88, and by means of the self test unit 62 the frequency and amplitude of the coil driver signal can be systematically varied.

In addition to the output signal of the unit 88, the current signal of the current sensor 72 and the current signal of the current sensor 86 are supplied to the multiplexer 94, which is connected upstream of the A/D converter 90. The sensor current signals are supplied, in this way, to the self-test unit 62 for evaluation. The complex impedance of the respective transmitter coil can be determined and monitored by means of the self-test unit 62 from the transmitter coil current and the transmitter coil voltage detected by current sensors 72 and 86. Also, a fault signal can be optionally output by way of the user interface 64 and 65. As illustrated in FIG. 1, the voltages of the transmitter coil are measured at sites 1, 3 and are supplied to the PAL element by way of the multiplexer 94 and the A/D converter 90.

Furthermore, the offset voltage of the receiver coil of the probe 11 can be monitored by means of the self-test unit 62 (Note: only difference coils have an offset voltage, which arises in any difference coil arrangement since two coils are never exactly identical).

The offset voltage can be eliminated from the receiver signal by means of a high-pass filter. The difference of the voltage before and after the high-pass filter then yields the offset voltage.

Advantageously, the self-test unit 62 is made such that the transmitter coil current and the receiver coil offset voltage are stored as a function of time allowing for observation of long-term changes of the transmitter coils and the receiver coils. This monitoring is especially important when the system is designed as an inductive particle counter because the coils cannot be easily dismounted and checked.

Furthermore, the self-test unit 62 is configured such that calibration of the signal processing electronics is enabled by means of a certified calibration standard 96 which can replace the coil 11. The calibration standard 96 is connected on the input side to the transmitter coil driver 70 and on the output side to the multiplexer 76 and to the amplifier 74. When the calibration standard 96 has several reference elements, such as, different resistances, which are switched over in the course of calibration, the calibration standard 96 has one terminal 98, for example an I²C bus, which is connected to the processor 60 and the self-test unit 62 for undertaking the corresponding switchovers of the reference elements.

Sites 2, 4 allow for direct measurement of the voltages upstream of the input channels of the amplifier 74 and of the unit 88. Thus, it is possible to directly measure the voltage drop with the calibration standard 96 which was set instead of the corresponding coil, for example.

It is preferable that the calibration standard has at least one RC element with at least one calibrated measurement resistance for checking the precision of the A/D converter of the signal processing electronics. The sampling frequency of the processor 60 can also be checked with the RC element by using the corner frequency of the RC element which is precisely known. The measurement resistance of the calibration standard 96 is a lowpass filter to suppress interference. As a reference element, the measurement resistance of the calibration standard 96 provides for a defined voltage at the input of the A/D converter 80 so that unwanted fluctuations of the sampling frequency are detected.

It is preferable that calibration be performed once a year.

The calibration standard 96 may be a separate unit independent of the measurement device and connected to the measurement device only during calibration. This example embodiment is advantageous because the calibration of the calibration standard can be easily checked by a certified calibration laboratory.

Alternatively, the calibration standard 96 can be made as a part of the measurement device such as a component provided on a board of the measurement device which is connected in place of the corresponding coil at need. This example embodiment has the advantage that the measurement device does not need to be opened for preparation of calibration. However, in this case, the calibration of the calibration standard cannot be checked.

The calibration standard 96 is helpful especially for calibration of the adjustable preamplifier 74. When the calibration standard 96 for economic reasons has only a single or only a few reference resistance values, it is possible to proceed as follows. The RC element of the calibration standard 96 obtains a fixed sinusoidal voltage from the transmitter coil driver 70. The fixed sinusoidal voltage is so large that a sinusoidal signal can be digitally converted with a desired accuracy by means of the A/D converter 80 in the least sensitive position of the amplifier 74. If the gain is increased by means of the PAL element 68, the sine is cut off at some time, and the truncated sine then can be reconstructed again via mathematical approximation, such as a adjustment theoretical calculation. As a result, the actual amplitude of the signal can be measured. The prerequisite for this method is that the electronics used do not have a latchup effect and the input stage of the A/D converter 80 is protected against destruction by overvoltage.

The following equation of the adjustment theoretical computation for a sine may be used:

$$A0*n + A1*[\sin(x)] + A2*[\cos(x)] = [yi]$$

$$A0*[\sin(x)] + A1*[\sin^2(x)] + A2*[\sin(x)*\cos(x)] = [yi*\sin(x)]$$

$$A0*[\cos(x)] + A1*[\sin(x)*\cos(x)] + A2*\cos^2(s)] = [yi*\cos(x)]$$

where yi is a measured value such that $y(i) = A0 + A1*\sin(x) + A2*\cos(x)$ and $x = 2*\pi*f*i*dt$, where f indicates the frequency. The brackets stand for summations over the running variable i from zero to n. Those measured values which are outside the allowable range, i.e., the "truncated" values, may not be used here. The value x represents the current angle, which need not be equidistant.

By computing the amount of A1 and A2, the original amplitude $A = SQRT(A1*A1 + A2*A2)$ and the phase offset $PHI = \arctan(A2/A1)$ are obtained.

It goes without saying that the described signal reconstruction can be used not only in the checking of the variable amplifier 74, but also in an eddy current test, if as a result of certain circumstances the receiver coil signals arise which overdrive the A/D converter. Ultimately, the measurement range can be expanded by this signal reconstruction using only software.

The relatively simple checking of the variable amplifier 74 described above allows for the storage and use of correction values for the respective gain, allowing for more economical amplifiers of the same quality.

There are resonance filters, like the resonance filter (or a combination of high-pass and low-pass filters) 78, allowing for operation with a variable transmitter frequency. The most favorable sampling frequency arising as a function of the velocity of the test piece, effective coil width, and transmitting frequency. As already described, in a self-test using variation of the frequency and amplitude of the input voltage, the corner frequencies and the edge steepness of the filters can be determined.

Changes of the sensor hardware, especially damage, can be ascertained early by the described impedance measurements of the transmitter and receiver windings using the self-test unit 62 so that test times with damaged sensor hardware can be avoided as much as possible. As a result, measurement becomes more reliable.

The described measurement of the receiver coil offset voltage by the self-test unit 62 enables early detection of overdriving problems, for example, in conjunction with certain test piece materials. This allows for preventive reactions to problems and increases in the reliability of the test.

The possibility of calibration of the system by means of the self-test unit 62 and the calibration standard 96 enables simple calibration of the system on site, eliminating the necessity of installation and dismounting of a test adapter in the system. As a result, production and servicing of the system is more economical, because an adaptation of a front end in a testing device is not needed.

The calibration standard 96, itself, if it is made as a separate unit, can of course also be calibrated at regular intervals by a certified calibration laboratory, as previously described.

Figure 2:
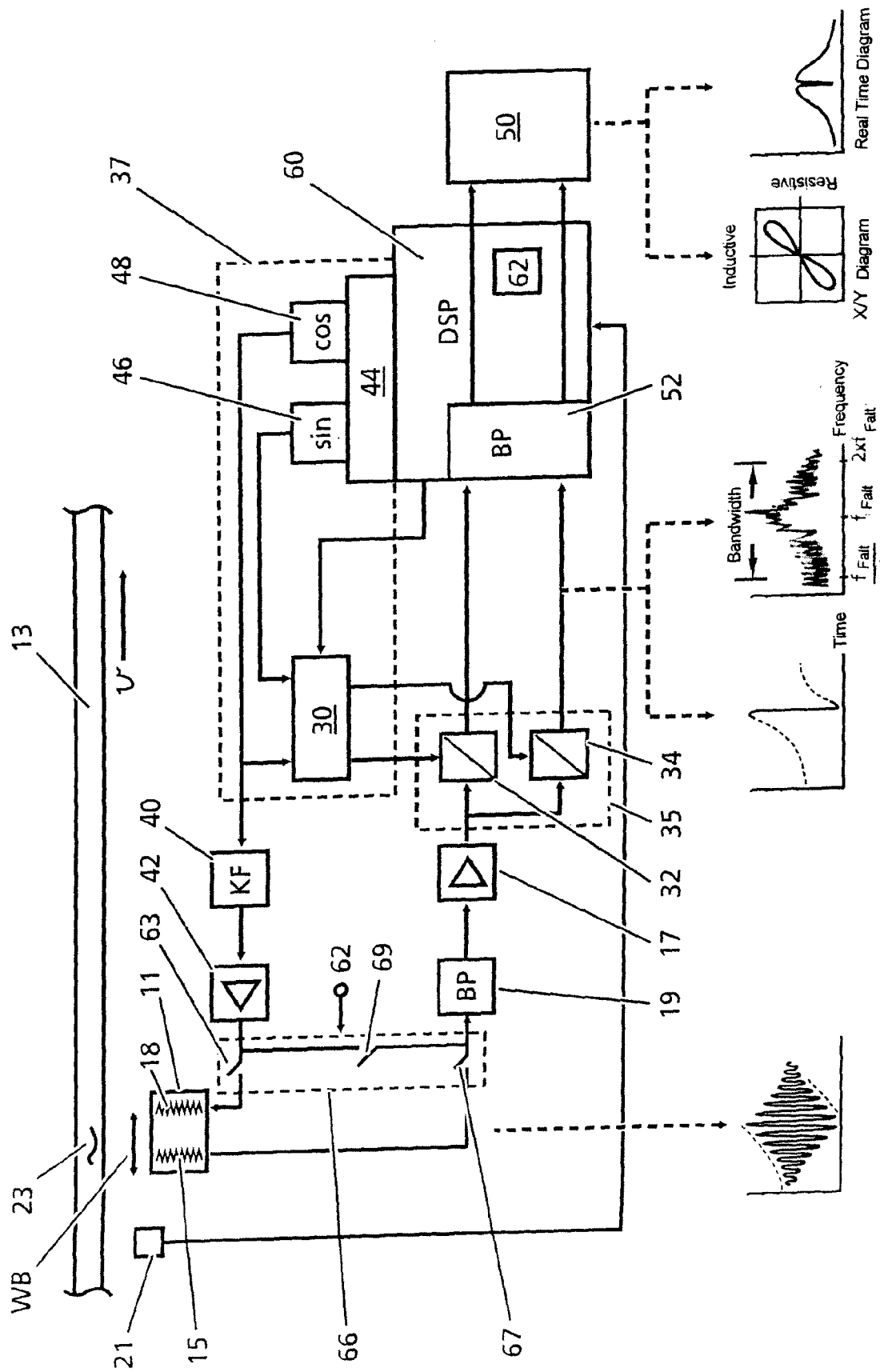
FIG. 2 is a block diagram of an aspect of the invention which is used for detecting faults in a moving test piece.

FIG. 2 illustrates a block diagram of an example of an inductive measurement device according to an aspect of the claimed invention which is used for detecting faults in a moving test piece and a digital demodulation method. Aside from the self-test function and signal reconstruction, this device is described in International Patent Application Publication WO 2006/007826 A1. Here, a test piece 13 in the form of a semi-finished industrial article, for example, a slab, which is tested when it moves linearly with a variable velocity v passed the probe 11. The velocity is detected with a velocity detector 21 which can deliver, for example, a signal essentially proportional to the velocity v. The signal can be, for example, a rectangular signal (possibly also two-track in order to be able to distinguish forward and backward) which contains one pulse, for example, per 5 mm advance of the test piece 13.

The probe 11 has a transmitter in the form of a transmitter coil 18 and a receiving coil 15. With an alternating electromagnetic field with at least one given carrier frequency, the transmitter coil 18 is used to induce eddy currents in the test piece 13. These eddy currents in turn induce an AC voltage in the receiving coil 15 which AC voltage acts as a probe signal and has a carrier oscillation with the carrier frequency of the transmitter coil 18. The amplitude and the phase of the probe signal is modulated by a fault 23 when the fault 23 travels into the effective width WB of the receiving coil 15. The receiving coil 15 is preferably made as a difference coil, i.e., a coil with two windings which are wound in the opposite direction, and react only to changes of the electrical properties due to the presence of a fault 23 of the test piece. Difference coils are suitable mainly for detection of sudden changes in the test piece 13. An absolute coil can also be used as the receiving coil 15 which comprises several windings wound in the same direction, and suitable especially for detection of long homogeneous changes in the test piece 13.

The voltage for the transmitter coil 18 can be produced by a binary signal produced by a timer unit 44 and delivered to a generator 48 as the input frequency which produces a rectangular signal or a sinusoidal signal which travels through the curve shaper 40 and then is amplified by a power amplifier 42 before being sent to the transmitter coil 18. Preferably, the signal has a sinusoidal shape and in the simplest case contains only a single carrier frequency, but measurements with several carrier frequencies at the same time and/or carrier signals which differ distinctly from sinusoidal oscillations are also possible. Typically the carrier frequency is in the range from 1 kHz to 5 MHz.

Fundamentally, the transmitter coil can also be operated with a digital signal based on the pulse duration modulation. This has the advantage of greatly reducing the power loss in the driver stage.

The probe signal received by the receiving coil 15 travels through a bandpass filter 19 and an adjustable preamplifier 17 before being supplied to an A/D converter stage 35. The bandpass filter 19 is used, on the one hand, as an (anti-) aliasing filter with respect to signal digitization by the A/D converter stage 35, and on the other hand, to mask out high frequency and low frequency noise signals. The adjustable preamplifier 17 is used to bring the amplitude of the analog probe signal to the amplitude optimally suitable for A/D converter stage 35.

The A/D converter stage 35 has two A/D converters 32, 34 which are connected in parallel and have high resolution with a resolution of at least 16 bits, preferably at least 22 bits. It is also preferable that the A/D converter stage 35 is able to carry out at least 500 A/D conversions per second. The A/D converters 32, 34 are preferably flash converters or SAR (successive approximation register) converters.

The version with two A/D converters is one example. It is important that the fault signal is orthogonally sampled, which may also be performed with only one converter.

The A/D converter stage 35 is triggered by a trigger means 37, which has the aforementioned timer unit 44, a cosine generator 48, a sine generator 46 located parallel to the cosine generator 48, and a frequency divider 30. The signal which has been generated by the cosine generator 48 and which has the frequency of the carrier frequency of the supply signal of the transmitter coil 18 is provided to the frequency divider 30. The signal of the sine generator 46 which corresponds to the signal of the cosine generator 48, but with a phase-shift of 90° thereto, is also provided to frequency divider 30. In the frequency divider 30 these two signals are divided with respect to their frequency by a whole number n. The corresponding frequency-reduced output signal is used to trigger the A/D converter 32 and the A/D converter 34. The selection of the number n for the divider 30 is undertaken by a digital signal processor 60 depending on the fault frequency, i.e., the quotient of the current velocity of the test piece v and the effective width WB of the receiving coil 15. Preferably, n is chosen to be inversely proportional to the main fault frequency in order for the trigger rate of the A/D converter stage 35 to be at least roughly proportional to the main fault frequency. This results in that if the effective width WB in the first approximation is assumed to be constant, at a higher test piece velocity v and thus a high fault frequency the analog probe signal is sampled more frequently.

Preferably, the divider 30 is made as a so-called PAL (Programmable Array Logic) component in order to ensure that the trigger signals arrive synchronously, to the output signal of the cosine generator 48 and the sine generator 46 without phase jitter at the A/D converter stage 35.

Due to the corresponding phase shift of the two input signals of the divider 30, the two A/D converters 32, 34 are also triggered with a fixed phase offset of 90°. In this way the analog probe signal can be evaluated in a two-component manner, i.e., with respect to amplitude and phase. It goes without saying that the phase delay between the trigger signal of the A/D converter signal 35 and the signal of the transmitter coil 18 should be as small as possible, and especially so-called phase jitter should also be avoided, i.e., the phase relations should be constant in time as exactly as possible.

With the illustrated trigger means 37, the analog probe signal is sampled by each A/D converter 32, 34 at most once per full wave of the carrier oscillation (in this case n is equal to 1). Depending on the current fault frequency, i.e., the velocity of the test piece v, n can be much larger than 1 so that sampling is performed only in each n-th full wave of the carrier oscillation.

As already mentioned, what matters is that sampling is taken orthogonally. When sampling is done at 0° and 90° the complex components of the fault signal are obtained. At 180° and 270° the same components are obtained, but in the inverse to those taken at 0° and 90°. By inverting these components an average can be formed and thus an increased sampling rate can be used. Such sampling methods have advantages with respect to noise and design of the input filter.

The demodulated, digital, two-channel output signal of the A/D converter stage 35 travels through a digital bandpass filter 52 which can be the signal processor 60. The digital bandpass filter 52 is used to mask out noise signals outside the bandwidth of the fault signal. For this purpose, the corner frequency of the high-pass filter (software filter) is preferably chosen such that it is less than one fourth of the fault frequency, while the corner frequency of the low-pass filter is preferably chosen such that it is at least twice the fault frequency to avoid masking out the signal portions which still contain information of the fault.

The digital bandpass 52 is clocked with the sampling rate of the A/D converter stage 35, i.e., the trigger rate. This has the advantage that the corner frequencies of the bandpass are automatically entrained with the fault frequency when the fault frequency changes, i.e., when the velocity of the test piece v changes, since the corner frequencies of a digital bandpass filter are proportional to the clock rate and the clock rate is automatically adapted to the change of the fault frequency by way of the sampling rate which is stipulated by the trigger unit 37.

This also applies analogously when the transmission frequency has been changed. This reduces the cost of digital filtration with respect to different types of filter stages.

The information necessary for determining the main fault frequency with respect to the effective width WB can be either manually input to the signal processor 60 made available directly by the probe 11, as described, for example, in European Patent Application No. 0 734 522 B1.

It goes without saying that the measurement system reacts analogously to the change of the fault frequency which is caused when the velocity v of the test piece remains constant, but the receiving coil 15 is replaced by another with a different effective width WB.

The useful signal, which is obtained after filtration by the digital bandpass filter 52, is evaluated in a known manner by an evaluation unit 50 in order to detect and locate faults 23 of the test piece 13. For detection both the amplitude information and the phase information of the fault signal is used.

In particular, for relatively large values of n, i.e., when only a relatively small number of full waves of the carrier oscillation are sampled, the transmitter coil 15 and/or the evaluation electronics, especially the signal processor 60, can be turned off or put on stand-by in order to reduce power consumption during the sampling pauses. Such capability is important especially for portable measurement devices.

In the processor 60 the self-test unit 62 for the monitoring and calibration functions named above in conjunction with FIG. 1 is implemented. Thus, the self-test unit 62 controls the switch arrangement 66 with three switches 63, 67, 69 in order to feed the signal for the transmitter coil 18 of the probe 11 bypassing the transmitter coil 18 and the receiver coil 15 directly as a periodic input signal into the signal processing, i.e., into the input of the bandpass filter 19.

Figure 3:
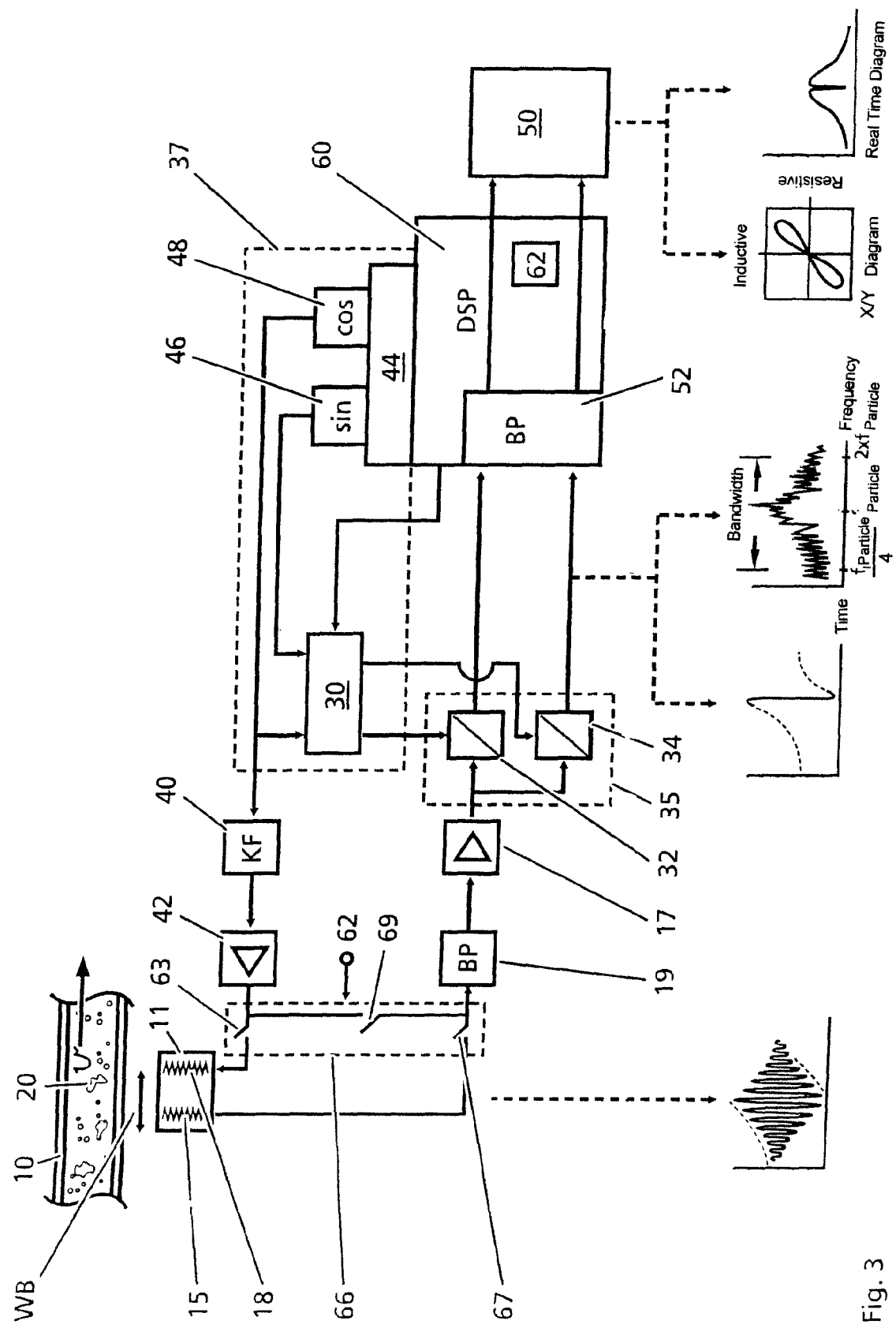
FIG. 3 is a block diagram of one example of an inductive measurement device according to an aspect of the invention which is used for detecting electrically conductive particles in a flowing liquid.
Figure 4:
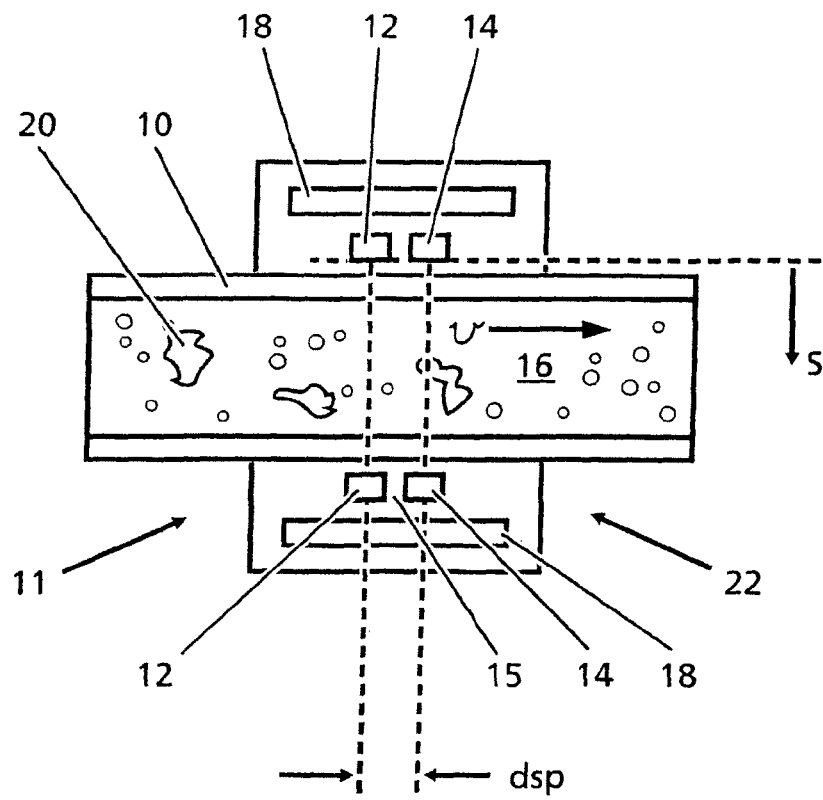
FIG. 4 schematically illustrates a longitudinal section through a pipe through which a liquid is flowing and which is provided with a transmitter and receiver coil for use with the measurement device as shown in FIG. 3.
Figure 5:
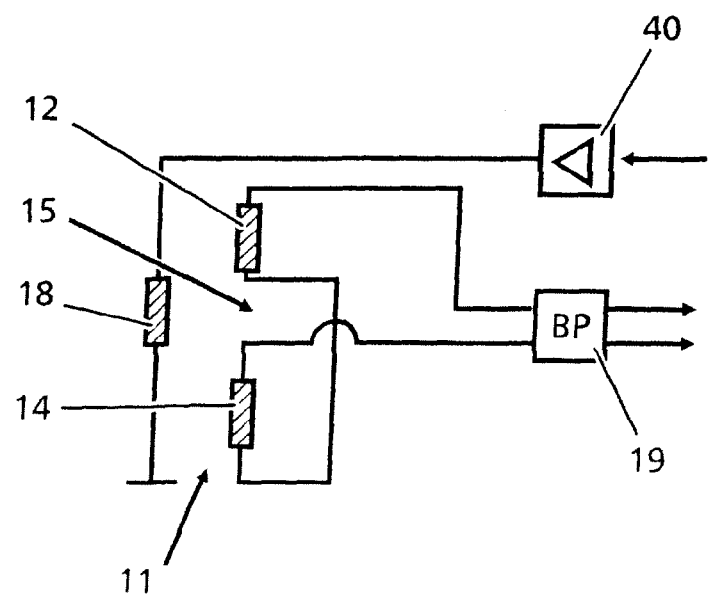
FIG. 5 is a block diagram of the wiring of the coils from FIG. 4.

FIGS. 3 to 5 show an example of an inductive measurement device according to an aspect of the claimed invention used to detect electrically conductive particles in a flowing liquid using a digital demodulation method. Aside from the self-test function, this device is described in U.S. Patent Application Publication No. 2009/0051350. Fundamentally, the signal processing, especially the signal reconstruction when the A/D converter is being overdriven, and the self-test functions are performed analogously to the above described approach shown in FIG. 2.

As shown in FIG. 4, a pipe segment 10 is surrounded by a first inductive receiver coil 12 and a second inductive receiver coil 14 which is spaced apart from the receiver coil 12 in the axial direction so that a liquid 16 flowing in the pipe segment 10 flows through the coils 12, 14 in the axial direction. The axial distance of the two coils 12, 14 and the axial dimensions of the coils 12, 14 are, for example, 2 mm. The two receiver coils 12, 14 are surrounded on the outside by a transmitting coil 18 which is located coaxially to the two coils 12, 14 and has a larger diameter than coils 12, 14. The axial dimensioning of the transmitter coil 18 is such that the two receiver coils 12, 14 are located completely within the transmitter coil 18. Preferably, the extension of the transmitter coil 18 in the axial direction is at least twice as great as the axial extension of the arrangement of the receiver coils 12, 14, i.e., the distance plus the axial extension of the coils 12, 14. The coils 12, 14, 18 are located in a housing 22 which surrounds the pipe segment 10 and form a probe 11.

Typically, the pipe segment 10 is part of the lubricant circuit of a machine, then, the liquid 16, for example, is a lubricant containing metal particles which are typically abrasion from moving parts of the machine. A typical value for the lubricant flow rate in the main flow is 10 liters/min. At much higher flow rates it is advantageous to measure a secondary flow, instead of the main flow.

As shown in FIG. 5, the two receiver coils 12, 14 are connected subtractively as a difference coil 15, i.e., they are wound in opposite directions, so that a voltage with the same amount but with opposite signs is induced in the two coils 12, 14. The transmitter coils 18 and the receiver coils 12, 14 form a transformer arrangement, where the transmitter coil 18 forms the primary side and the receiver coils 12, 14 form the secondary side. The transformer core is formed by the materials or media fed through the coils 12, 14, 18, e.g., air, the housing 22, the pipe 10, and the liquid 16 with the particles 20.

The impedance difference of the coils 12, 14 caused by the particles 20, i.e. the difference of the impedance of the two coils 12, 14 caused by the instantaneous presence of a particle 20 in one of the two coils 12, 14 (the particles 20 are much smaller than the distance of the coils 12, 14), is imaged by the measurement signal output by the coils 12 and 14.

FIG. 3 shows an example of the structure of the eddy current measurement device that uses the probe 11 according to an aspect of the present invention.

The transmitter coil 18 is used, by means of an alternating electromagnetic field with at least one given carrier frequency, to induce eddy currents in the particles 20, which in turn induce an AC voltage that acts as the probe signal in the receiving coil 15 which is a difference coil. The induced voltage in the receiver coil has a carrier oscillation with the carrier frequency of the transmitter coil 18. The amplitude and the phase of the probe signal are modulated by a particle 20 when the latter travels into the effective width WB of the receiving coil 15.

The voltage of the transmitter coil 18 can be produced, for example, by a binary signal produced by a timer unit 44 input to a generator 48 producing a rectangular signal and a sinusoidal signal, which travels through the curve shaper 40 and then is amplified by a power amplifier 42 before being sent to the transmitter coil 18. Preferably the signal has a sinusoidal shape and in the simplest case contains only a single carrier frequency, but may also contain several carrier frequencies at the same time and/or carrier signals which differ distinctly from sinusoidal oscillations. Typically the carrier frequency is in the range from 5 kHz to 1 MHz.

The probe signal received by the receiving coil 15 travels through a bandpass filter 19 and an adjustable preamplifier 17 before being supplied to an A/D converter stage 35. The bandpass filter 19 is used, on the one hand, by means of a low-pass filter as an (anti-aliasing) filter with respect to signal digitization by the A/D converter stage 35, and on the other hand, by means of a high-pass to mask out low frequency noise signals. The adjustable preamplifier 17 is used to bring the amplitude of the analog probe signal to the amplitude optimally suitable for the A/D converter stage 35.

The A/D converter stage 35 has two A/D converters 32, 34 which are connected in parallel and have high resolution with a resolution of at least 16 bits, preferably at least 22 bits, and are able to carry out at least 500 A/D conversions per second. The A/D converters 32, 34 are preferably made as flash converters or SAR (successive approximation register) converters.

If offset voltage compensation takes place by means of an additional D/A converter and subtractor, a resolution of the A/D converter of 12 bits is sufficient.

The A/D converter stage 35 is triggered by a trigger means 37 which has the aforementioned timer unit 44, the cosine generator 48, the sine generator 46 which is located parallel to the cosine generator 48, and the frequency divider 30. A signal is provided to the frequency divider 30. The signal has been generated by the cosine generator 48 and has the frequency of the carrier frequency of the supply signal of the transmitter coil 18, and the signal of the sine generator 46 which corresponds to the signal of the cosine generator 48, but which is phase-shifted by 90° to with respect to the signal of the cosine generator 48. In the frequency divider 30 these two signals are divided with respect to their frequency by a whole number n. The corresponding frequency-reduced output signal is used to trigger the A/D converter 32 and the A/D converter 34. The selection of the number n for the divider 30 is undertaken by a digital signal processor 60 depending on the particle frequency, which is the quotient of the flow velocity v of the liquid 16, i.e. the velocity v of the particles 20, and the effective width WB of the receiving coil 15. Preferably, n is chosen to be inversely proportional to the particle frequency in order for the trigger rate of the A/D converter stage 35 to be at least roughly proportional to the particle frequency. Therefore, if the effective width WB in the first approximation is assumed to be constant, at a higher flow/particle velocity v and thus higher particle frequency the analog probe signal is sampled more frequently.

Preferably, the divider 30 is made as a so-called PAL (Programmable Array Logic) component in order to ensure that the trigger signals arrive with minimum delay, i.e. as synchronously as possible with the output signal of the cosine generator 48 and the sine generator 46 and without phase jitter at the A/D converter stage 35.

Due to the corresponding phase shift of the two input signals of the divider 30, the two A/D converters 32, 34 are also triggered with a fixed phase offset of 90°. In this way, the analog probe signal can be evaluated in a two-component manner, i.e., both with respect to amplitude and phase. It goes without saying that the phase delay between the trigger signal of the A/D converter signal 35 and the signal of the transmitter coil 18 should be as small as possible, and especially so-called phase jitter should also be avoided, i.e., the phase relations should be as constant in time as possible.

It is ensured that the analog probe signal is sampled by each A/D converter 32 and 34 at most once per full wave of the carrier oscillation (in this case n is equal to 1) with the illustrated trigger means 37. Depending on the current particle frequency, i.e., the velocity of the liquid v, n however can be much greater than 1 so that sampling only takes place at each n-th full wave of the carrier oscillation.

Since sampling takes place at most once per full wave per A/D converter 32, 34, the frequency of the carrier oscillation, i.e., the carrier frequency, is eliminated from the digital signal by this undersampling, i.e., demodulation of the analog probe signal takes place by means of undersampling.

Preferably, n is chosen such that a noticeable particle signal is observed in the time interval. That is, a time interval is chosen such that one point of a particle 20 moves through the effective width WB of the receiving coil 15 in this time interval which corresponds essentially to the inverse of the main particle frequency, which is at least 5, preferably at least 20 samples are taken by each A/D converter 32 and 34 to obtain enough information contained in the particle signal sufficient for reliable particle detection. Generally however, not more than 50, at most 100, samplings will be necessary during this time interval, a minimum of 10 samplings.

The frequency of the carrier oscillation should be chosen such that it is at least ten times the particle frequency, since otherwise the particle signal is carried by too few full waves of the carrier oscillation and the reproducibility of particle detection becomes a problem.

The demodulated, digital, two-channel output signal of the A/D converter stage 35 travels through a digital bandpass filter 52 which may be the signal processor 60 and which is used to mask out noise signals which are outside the bandwidth of the particle signal. For this purpose, the corner frequency of the high-pass filter is preferably chosen such that the corner frequency is less than one fourth of the particle frequency, while the corner frequency of the low-pass filter is preferably chosen such that it is at least twice the particle frequency in order to avoid masking out the signal portions which still contain information with respect to particle passage.

The digital bandpass filter 52 is clocked with the sampling rate of the A/D converter stage 35, i.e., the trigger rate; this entails the major advantage that the corner frequencies of the bandpass filter when the particle frequency changes, i.e., when the velocity of the particles v changes, are automatically entrained with the particle frequency since the corner frequencies of a digital bandpass filter are proportional to the clock rate which is automatically adapted to the change of the particle frequency by way of the sampling rate which is stipulated by the trigger unit 37.

The information which is necessary for determining the main particle frequency with respect to the effective width WB can be either input manually to the signal processor 60 or provided directly by the measurement head 11, as is described, for example, in European Patent Application No. 0 734 522 B1 and corresponding to International Patent Application Publication. No. WO 95/16912.

It goes without saying that the measurement system reacts analogously to the change of the particle frequency which is caused when the particle velocity v is kept constant, but the receiving coil 15 is replaced by another with a different effective width WB.

In particular, for relatively large values of n, i.e., when only a relatively small number of full waves of the carrier oscillation at all is sampled, for example the transmitter coil 18 and/or the evaluation electronics, i.e., especially the signal processor 60, can be turned off or put on stand-by during the sampling pauses in order to reduce power consumption. This is important especially for portable measurement devices.

The useful signal obtained after filtration by the digital bandpass filter 52 is evaluated in an evaluation unit 50 in order to detect the passage of particles 20 using the amplitude and phase information of the particle signal.

Advantageously, the evaluation unit 50 is made such that the detected particle passages are counted so that conclusions can be made about the particle concentration in the liquid 16, and the state of the machine.

Fundamentally, in a difference coil, as a result of difference formation (the individual coils of the difference coil are never exactly alike in practice), the so-called coil offset voltage arises that can exceed the actual fault signal by several orders of amplitude, for example, by 100 to 30000 times. The resulting relatively large amplitude of the receiver coil signal compared to the actual useful signal imposes high demands on the electronics, especially on the resolution of the A/D converter.

Monitoring and calibration functions, which are named above in conjunction with FIG. 1, are implemented in the self-test unit 62 of the processor 60. Thus, the self-test unit 62 controls the switch arrangement 66 with three switches 63, 67, 69 in order to feed the signal for the transmitter coil 18 of the probe 11 by bypassing the transmitter coil 18 and the receiver coil 15 directly as a periodic input signal into the signal processing, i.e., into the input of the bandpass filter 19.

What is claimed is:

1. A method for detecting electrically conductive particles in a liquid flowing in a pipe segment with a velocity (v), comprising
    exposing the liquid to a plurality of periodic alternating electromagnetic fields with a transmitter coil arrangement in order to induce a plurality of eddy currents in the particles;
    detecting a periodic electrical signal according to the plurality of eddy currents with a receiver coil arrangement, such that the periodic electrical signal has a carrier oscillation where at least one of an amplitude and a phase is modulated by the particles when the particles travel into an effective width of the receiver coil arrangement;

digitizing the receiver coil signal with an A/D converter stage;

producing a useful signal from the digitized receiver coil signal with a signal processing unit;

evaluating the useful signal with an evaluation unit in order to detect a passage of electrically conductive particles in the pipe segment;

when through monitoring a curve shape of the digitized received coil signal overdriving of the A/D converter stage by the receiver coil signal is ascertained by the signal processing unit and a part of the receiver coil signal is being truncated by the A/D converter stage reconstructing the received coil signal with a mathematical approximation in the digitized receiver coil signal.

2. A method as claimed in claim 1, wherein the truncated part of the receiver coil signal is reconstructed with a adjustment theoretical computation.

3. A method as claimed in claim 1, wherein the receiver coil signal has a sinusoidal amplitude characteristic.

4. A method as claimed in claim 1, further comprising systematically and quantitatively checking, either automatically or upon external request, at least one of a signal processing functions of the signal processing unit, the transmitter coil arrangement, and the receiver coil arrangement, and replacing at least one of the transmitter coil arrangement and the receiver coil arrangement with the calibration standard in order to calibrate the signal processing unit.

5. A method as claimed in claim 4, wherein the systematic and quantitative checking of said at least one of the signal processing functions of the signal processing unit, the transmitter coil arrangement, and the receiver coil arrangement is undertaken automatically each time the signal processing unit starts up.

6. A method as claimed in claim 4, wherein the calibration standard comprises at least one RC element and the signal processing unit, and an adjustable preamplifier for the receiver coil signal, wherein the preamplifier is checked by a fixed sinusoidal voltage sent to the RC element, such that an amplitude is chosen in a least sensitive setting of the preamplifier and a sinusoidal signal can be digitally converted with the desired accuracy with the A/D converter stage so that at higher gain of the preamplifier, the sinusoidal signal is overdriven, and determining an actual signal amplitude by means of mathematical reconstruction of part of the receiver coil signal truncated by the A/D converter stage at a more sensitive setting of the preamplifier.

7. A device for detecting electrically conductive particles in a liquid flowing in a pipe segment with a velocity (v), comprising:

a transmitter coil arrangement with at least one transmitter coil for exposing the liquid to periodic alternating electromagnetic fields to induce a plurality of eddy currents in the particles;

a receiver coil arrangement with at least one receiver coil for detecting a periodic electrical signal, according to the induced eddy currents, such that the periodic electrical signal has a carrier oscillation where at least one of an amplitude and a phase is modulated by the particles when the particles travel into an effective width of the receiver coil arrangement;

a signal processing unit for producing a useful signal from a receiver coil signal; and an evaluation unit for evaluating the useful signal for purposes of detecting the passage of electrically conductive particles in the pipe segment, wherein the signal processing unit reconstructs the part of the receiver coil signal truncated by an A/D converter stage with a mathematical approximation in the digitized receiver coil signal when overdriving of the A/D converter stage by the receiver coil signal is ascertained by monitoring a curve shape of the digital receiver coil signal by the signal processing unit.

* * * * *